United States Patent
Eguchi et al.

(10) Patent No.: US 9,840,485 B1
(45) Date of Patent: Dec. 12, 2017

(54) BISFURAN DIHALIDE, METHOD FOR PRODUCING BISFURAN DIHALIDE, AND METHOD FOR PRODUCING BISFURAN DIACID, BISFURAN DIOL OR BISFURAN DIAMINE USING BISFURAN DIHALIDE

(71) Applicants: SEKISUI CHEMICAL CO., LTD., Osaka (JP); Colorado State University Research Foundation, Fort Collins, CO (US)

(72) Inventors: Yuji Eguchi, Tsukuba (JP); Eugene Y.-X. Chen, Fort Collins, CO (US); Lu Wang, Fort Collins, CO (US)

(73) Assignees: SEKISUI CHEMICAL CO., LTD., Osaka (JP); COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 0 days.

(21) Appl. No.: 15/277,297

(22) Filed: Sep. 27, 2016

(51) Int. Cl.
C07D 307/36 (2006.01)
C07D 307/68 (2006.01)
C07D 307/42 (2006.01)
C07D 405/06 (2006.01)
C07D 307/52 (2006.01)

(52) U.S. Cl.
CPC ......... *C07D 307/36* (2013.01); *C07D 307/42* (2013.01); *C07D 307/52* (2013.01); *C07D 307/68* (2013.01); *C07D 405/06* (2013.01)

(58) Field of Classification Search
None
See application file for complete search history.

(56) References Cited

PUBLICATIONS

Cresp, T.M. 8,11-Imino-2,5:14,17-diepoxy[17]annulenone. J.C.S. Chem. Comm. 1972, 807-808.*
Vishwanath Gaitonde et al., "Bio-Based Bisfuran: Synthesis, Crystal Structure and Low Molecular Weight Amorphous Polyester", Tetrahedron Lett., Jul. 23, 2014; 55(30): 4141-4145.
M. Abid et al., "Preparation of New Poly(ester triazole) and Poly(amide triazole) by 'Click Chemistry'", Polymer Science, Ser. B, (2014), vol. 56, Nos. 3-4, pp. 290-297.
Irina Delidovich et al., "Alternative Monomers Based on Lignocellulose and Their Use for Polymer Production", Chem. Rev., 2016, 116 (3), pp. 1540-1599.

* cited by examiner

*Primary Examiner* — Samantha Shterengarts
(74) *Attorney, Agent, or Firm* — Wenderoth, Lind & Ponack, L.L.P.

(57) ABSTRACT

A bisfuran dihalide having a structure represented by the following formula (1):

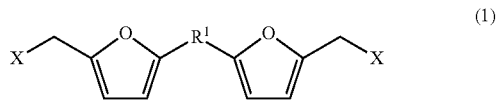

(1)

wherein $R^1$ is a divalent hydrocarbon group represented by $-CR^2R^3-$ (wherein each of $R^2$ and $R^3$ independently represents a hydrogen atom or a monovalent hydrocarbon group, and $R^2$ and R3 may together form a cyclic structure), or a carbonyl group ($-C(=O)-$); and each X independently represents a halogen atom.

15 Claims, No Drawings

BISFURAN DIHALIDE, METHOD FOR PRODUCING BISFURAN DIHALIDE, AND METHOD FOR PRODUCING BISFURAN DIACID, BISFURAN DIOL OR BISFURAN DIAMINE USING BISFURAN DIHALIDE

TECHNICAL FIELD

The present invention relates to a bisfuran dihalide, a method for producing a bisfuran dihalide, and a method for producing a bisfuran diacid, a bisfuran diol or a bisfuran diamine using the bisfuran dihalide.

DESCRIPTION OF RELATED ART

In recent years, technical development of bio-based polymers produced from renewable biomass as a raw material is in progress as a means to reduce consumption of fossil fuels such as petroleum and coal to thereby contribute to mitigation of global warming. As the monomer materials in obtaining bio-based polymers, bisfuran compounds (polymerizable monomers) having a structure where two furan rings are bound together through a divalent hydrocarbon group or the like has been attracting attention as bio-based raw materials having a structure similar to the bisphenol type compounds. As the aforementioned bisfuran compounds, a bisfuran diacid, a bisfuran diol, a bisfuran diamine and the like are known.

As to the synthesis of a bisfuran diol, there is a known method that uses, as a starting material, furfural obtained by hydrolyzing a biomass-derived hemicellulose, and include (1) converting an aldehyde group of furfural to 1,3-dithiolane, (2) dimerizing the obtained compound by Friedel-Crafts alkylation reaction, (3) subjecting the obtained dimer to dedithioacetalization to obtain a bisfuran dialdehyde, and (4) further converting this compound to a bisfuran diol (Non-Patent Document 1). As to the synthesis of a bisfuran diacid, there is a known method that, when viewed as starting from furfural as in the above case, include (1) oxidizing furfural to obtain a furan carboxylic acid, (2) esterifying the obtained furan carboxylic acid to obtain an ethyl ester of furan carboxylic acid, (3) subjecting the obtained ester to a condensation reaction (catalyzed by an acid catalyst) with acetone to obtain a diethyl ester of bisfuran dicarboxylic acid, and (4) hydrolyzing the diester to obtain a bisfuran dicarboxylic acid (Non-Patent Document 2). As to the synthesis of a bisfuran diamine, a method in which furfuryl amine is dimerized by reaction with a ketone is known (Non-Patent Document 3).

Thus, these bisfuran compounds are synthesized through different intermediates. However, for streamlining the overall process of synthesizing various bisfuran compounds, the development of a common intermediate has been desired.

DOCUMENTS OF RELATED ART

Patent Documents

[Non-Patent Document 1] Vishwanath Gaitonde et al., "Bio-Based Bisfuran: Synthesis, Crystal Structure and Low Molecular Weight Amorphous Polyester", Tetrahedron Lett. 2014 Jul. 23; 55(30): 4141-4145
[Non-Patent Document 2] Abid, M., Aden Ali, M., Bernard, J. et al., "Preparation of new poly(ester triazole) and poly(amide triazole) by 'click chemistry'", Polym. Sci. Ser. B (2014) 56: 290
[Non-Patent Document 3] Irina Delidovich et al., "Alternative Monomers Based on Lignocellulose and Their Use for Polymer Production", Chem. Rev., 2016, 116 (3), pp 1540-1599

SUMMARY OF THE INVENTION

Problems to be Solved by the Invention

The present invention has been made in view of the aforementioned situation, and the object of the present invention is to provide a compound which can be used as a common intermediate for various bio-based bisfuran compounds (polymerizable monomers) such as a bisfuran diacid, a bisfuran diol and a bisfuran diamine.

Means to Solve the Problems

[1] A bisfuran dihalide having a structure represented by the following formula (1):

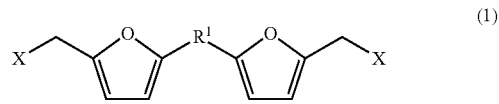

wherein $R^1$ is a divalent hydrocarbon group represented by $-CR^2R^3-$ (wherein each of $R^2$ and $R^3$ independently represents a hydrogen atom or a monovalent hydrocarbon group, and $R^2$ and $R^3$ may together form a cyclic structure), or a carbonyl group ($-C(=O)-$); and each X independently represents a halogen atom.

[2] The bisfuran dihalide according to [1], wherein each of $R^2$ and $R^3$ is independently a monovalent hydrocarbon group.

[3] The bisfuran dihalide according to [1], wherein each X is a bromine atom.

[4] A method for producing the bisfuran dihalide of any one of [1] to [3], comprising reacting a bisfuran having a structure represented by following formula (2) and a halogenating agent:

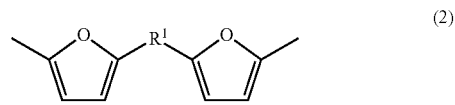

wherein $R^1$ is the same as $R^1$ in the formula (1).

[5] A method for producing a bisfuran diacid having a structure represented by formula (3) below, comprising oxidizing the bisfuran dihalide of any one of [1] to [3]:

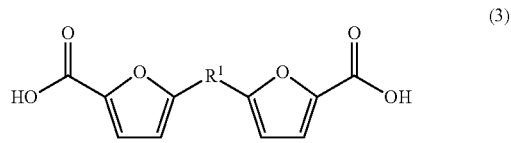

wherein $R^1$ is the same as $R^1$ in the formula (1).

[6] A method for producing a bisfuran diol having a structure represented by formula (4) below, comprising hydrolyzing the bisfuran dihalide of any one of [1] to [3]:

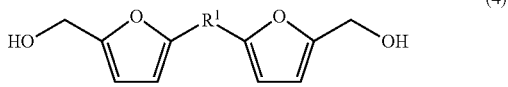

wherein $R^1$ is the same as $R^1$ in the formula (1).

[7] A method for producing a bisfuran diamine having a structure represented by formula (5) below, using the bisfuran dihalide of any one of [1] to [3] as a starting material:

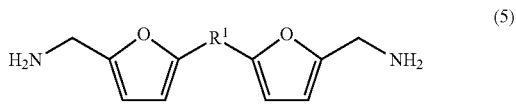

wherein $R^1$ is the same as $R^1$ in the formula (1).

Effect of the Invention

According to the present invention, it becomes possible to provide a compound which can be used as a common intermediate for various bio-based bisfuran compounds (polymerizable monomers) such as a bisfuran diacid, a bisfuran diol and a bisfuran diamine.

EMBODIMENTS FOR CARRYING OUT THE INVENTION (Bisfuran Dihalide)

According to one embodiment of the present invention, there is provided a bisfuran dihalide having a structure represented by the following formula (1):

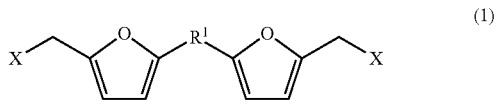

In the formula (1), $R^1$ is a divalent hydrocarbon group represented by —$CR^2R^3$— (wherein each of $R^2$ and $R^3$ independently represents a hydrogen atom or a monovalent hydrocarbon group, and $R^2$ and $R^3$ may together form a cyclic structure), or a carbonyl group (—C(═O)—).

$R^2$ and $R^3$ may be the same or different; however, from the viewpoint of readiness of synthesis of bisfuran dihalide, both of $R^2$ and $R^3$ are preferably a monovalent hydrocarbon group. Examples of monovalent hydrocarbon groups include an alkyl group having 1 to 12 carbon atoms, a cycloalkyl group having 5 to 12 carbon atoms, a cycloalkylalkyl group having 6 to 12 carbon atoms, and an aryl group having 6 to 12 carbon atoms. $R^3$ may be further substituted with a hydroxy group, namely, $R^3$ may be a hydroxyalkyl group. The alkyl group may be either linear or branched, and each of the cycloalkyl group, the cycloalkylalkyl group and the aryl group may have a substituent such as a lower alkyl group on the ring thereof.

Further, $R^2$ and $R^3$ may be bonded to each other to form a ring structure. For example, $R^2$ and $R^3$ may be bonded to each other such that $R^1$ has a cyclohexane ring structure.

Examples of the alkyl group include a methyl group, an ethyl group, a propyl group, an isopropyl group, a butyl group, an isobutyl group, a pentyl group, a hexyl group, a heptyl group, an octyl group, a nonyl group, and a decyl group. Examples of the cycloalkyl group include a cyclopropyl group, a cyclobutyl group, a cyclopentyl group, a cyclohexyl group, cycloheptyl group, cyclooctyl group, a cyclononyl group, a cyclodecyl group, a cycloundecyl group, and a cyclododecyl group. Examples of the cycloalkylalkyl group include a cyclopropylmethyl group, a cyclobutylmethyl group, a cyclopentylmethyl group, a cyclohexylmethyl group, a cycloheptylethyl group, and a cyclooctylethyl group. Examples of the aryl group include a phenyl group, a tolyl group, an ethylphenyl group, a xylyl group, a cumenyl group, a mesityl group, o-, m- and p-methoxyphenyl groups, o-, m- and p-ethoxyphenyl group, naphthyl groups (a 1-naphthyl group and a 2-naphthyl group, etc.), and a biphenyl group.

Among those exemplified above as $R^2$ and $R^3$, a methyl group, an ethyl group, an isobutyl group, a phenyl group and the like are preferable due to the availability of raw materials and the ease in synthesis.

In the formula (1), each X independently represents a halogen atom. Examples of the halogen atom include fluorine, chlorine, bromine, and iodine. Among these, chlorine, bromine and iodine are preferred, and bromine is more preferred.

The two X may be the same or different; however, from the viewpoint of readiness of synthesis of bisfuran dihalide, both X are preferably the same.

(Method for Producing a Bisfuran Dihalide)

Next, explanation is made on the method for producing a bisfuran dihalide.

The bisfuran dihalide of the present invention can be produced by a method including reacting a bisfuran having a structure represented by following formula (2) with a halogenating agent (hereinafter, this reaction is frequently referred to as a "halogenating reaction"):

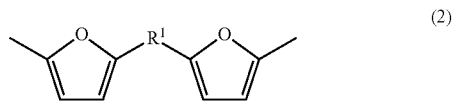

wherein $R^1$ is the same as $R^1$ in the formula (1).

The aforementioned bisfuran can be produced by a known method. For example, a bisfuran with $R^1$ being an isopropylidene group (i.e., 5,5'-(propane-2,2-diyl)bis(2-methylfuran) can be obtained by reacting 2-methylfuran and acetone in accordance with a known method.

As the aforementioned halogenating agent, any of conventional halogenating agents can be used. Examples of the halogenating agent include fluorinating agents such as fluorine ($F_2$), fluoroxytrifluoromethane, xenon difluoride, perchloryl fluoride, caesium fluorosulfate, acetyl hypofluorite, N-fluorosulfonamide, diethylaminotrifluorosulfur, N-fluoropyridinium, N-fluoro-2,6-di(methoxycarbonyl)pyridinium, N-fluoro-3,5-dichloropyridinium, and N-fluoro-2,4,6-trimethylpyridinium; chlorinating agents such as chlorine ($Cl_2$), thionyl chloride, N-chlorosuccinimide, cupric chloride, sulfuryl chloride, trichloroisocyanuric acid, titanium tetrachloride, 2,3,4,5,6,6-hexachloro-2,4-cyclohexadienone, 2,3,4,4,5,6-hexachloro-2,5-cyclohexadienone, N-chlorotriethyl ammonium chloride, and benzeneselenenyl chloride; brominating agents such as bromine ($Br_2$), hydrogen bromide, N-bromosuccinimide (NBS), cupric bromide, tetramethylammonium tribromide, trifluoroacetyl hypobromite, dibromoisocyanuric acid (DBI), 2,4,4,6-tetrabromo-2,5-cyclohexadienone, and 2,4-diamino-1,3-thiazole hydrotribromide; iodinating agents such as iodine ($I_2$), iodine chloride (ICl), 1,3-diiodo-5,5-dimethyl hydantoin, trifluoroacetyl hypoiodite, ethylene iodine chloride, and N-iodosuccinimide. Among these, N-chlorosuccinimide, N-bromosuccinimide, and N-iodosuccinimide are preferred.

The amount of the halogenating agent is preferably 2.0 to 4.0 mol, more preferably 2.1 to 3.5 mol, most preferably 2.2 to 3.0 mol, per 1 mol of the bisfuran represented by the formula (2) as a substrate.

The aforementioned halogenating reaction is generally performed in a solvent. Examples of the solvent used in the halogenation reaction include hydrocarbons such as heptane, hexane, cyclohexane, pentane, toluene, and xylene; ethers such as diethyl ether, tetrahydrofuran, 1,4-dioxane, ethylene glycol dimethyl ether, anisole, methyl tert-butyl ether, and diisopropyl ether; and halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methyl pyrrolidone; esters such as ethyl acetate, and methyl acetate; sulfoxides such as dimethyl sulfoxide; nitriles such as acetonitrile, and propionitrile; and mixtures thereof.

The aforementioned halogenation reaction may be performed in the presence of a radical initiator. Examples of the radical initiator include 2,2'-azobisisobutyronitrile (AIBN), 1,1'-azobis(cyclohexane-1-carbonitrile) (V-40) and benzoyl peroxide (BPO).

The amount of the radical initiator is preferably 0.01 to 0.5 mol, more preferably 0.02 to 0.4 mol, most preferably 0.05 to 0.3 mol, per 1 mol of the aforementioned bisfuran.

The preferable reaction conditions for the halogenation reaction are as follows. The reaction temperature is preferably −50 to 150° C., more preferably −30 to 120° C., still more preferably from 0 to 100° C.

According to another embodiment of the present invention, there is provided a method for producing a bisfuran diacid having a structure represented by formula (3) below, comprising oxidizing the aforementioned bisfuran dihalide (hereinafter, this reaction is sometimes referred to as a "diacid synthesis reaction"):

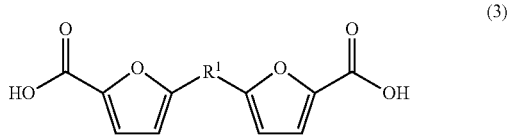

(3)

wherein $R^1$ is the same as $R^1$ in the formula (1).

The aforementioned oxidizing reaction may be performed in the presence of an alkali metal hydroxide. Examples of the alkali metal hydroxide include hydroxides of alkali metals such as sodium, potassium, cesium, and lithium. Among these hydroxides, sodium hydroxide is especially preferred.

The amount of the alkali metal hydroxide is preferably 2 to 100 mol, more preferably 3 to 90 mol, most preferably 4 to 80 mol, per 1 mol of the aforementioned bisfuran dihalide.

Further, the aforementioned diacid synthesis reaction may be performed in the presence of an oxidizing agent such as manganese compounds, e.g., $KMnO_4$ and activated manganese oxide; chromium compounds, e.g., chromium (IV) oxide and pyridinium dichromate; and peroxides, e.g., hydrogen peroxide and organic peroxides. The amount of the oxidizing agent is preferably 2 to 20 mol, more preferably 3 to 15 mol, most preferably 4 to 10 mol, per 1 mol of the aforementioned bisfuran dihalide.

The diacid synthesis reaction is generally performed in water. The water may be used in the form of a mixture thereof with a hydrophilic solvent. Examples of the hydrophilic solvent include dimethyl sulfoxide, dimethylformamide, dimethylacetamide, 1,4-dioxane, tetrahydrofuran, methanol and ethanol.

The preferable reaction conditions for the diacid synthesis reaction are as follows. The reaction temperature is preferably −20 to 100° C., more preferably 0 to 80° C., still more preferably from 10 to 60° C.

The obtained bisfuran diacid can be isolated and washed by a known method.

According to still another embodiment of the present invention, there is provided a method for producing a bisfuran diol having a structure represented by formula (4) below, comprising hydrolyzing the aforementioned bisfuran dihalide (hereinafter, this reaction is frequently referred to as a "diol synthesis reaction"):

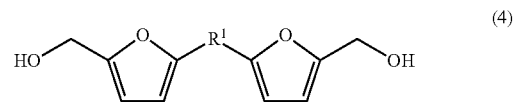

(4)

wherein $R^1$ is the same as $R^1$ in the formula (1).

For example, the aforementioned hydrolysis may be performed in the presence of a carbonate salt of an alkali metal. Examples of the carbonate salt of an alkali metal include sodium carbonate ($Na_2CO_3$) and potassium carbonate ($K_2CO_3$).

The amount of the carbonate salt of an alkali metal is preferably 2.0 to 6.0 mol, more preferably 2.0 to 5.0 mol, most preferably 2.0 to 4.0 mol, per 1 mol of the aforementioned bisfuran dihalide.

The diol synthesis reaction is generally performed in water. The water may be used in the form of a mixture thereof with a hydrophilic solvent. Examples of the hydrophilic solvent include dimethyl sulfoxide, dimethylformamide, dimethylacetamide, 1,4-dioxane, tetrahydrofuran, methanol and ethanol.

The preferable reaction conditions for the diol synthesis reaction are as follows. The reaction temperature is preferably −20 to 100° C., more preferably 0 to 80° C., still more preferably from 10 to 60° C.

The obtained bisfuran diol can be isolated and washed by a known method.

According to still another embodiment of the present invention, there is provided a method for producing a bisfuran diamine having a structure represented by formula (5) below, using the aforementioned bisfuran dihalide as a starting material:

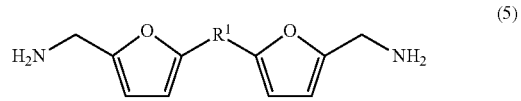

(5)

wherein $R^1$ is the same as $R^1$ in the formula (1).

With respect to the specific method for producing the bisfuran diamine, there is no particular limitation as long as the halogen atoms of the bisfuran dihalide can be replaced with amino groups (—NH$_2$). For example, the production can be carried out following the reaction scheme represented by formula (6) below.

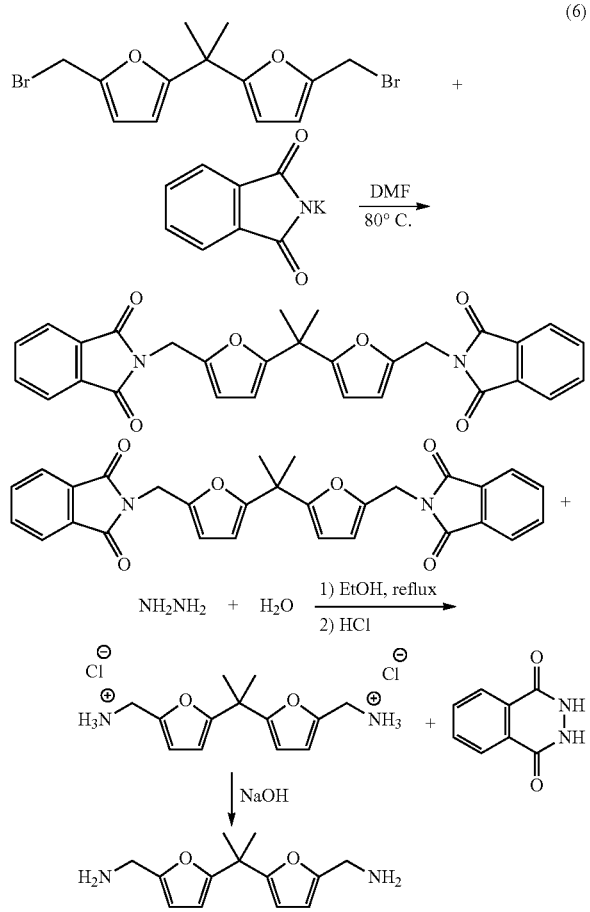

(6)

EXAMPLES

Hereinbelow, the present invention will be described in more detail with reference to the Examples which, however, should not be construed as limiting the scope of the present invention.

In the following Examples and Comparative Examples, the measurements by $^1$H-NMR and $^{13}$C-NMR were carried out using Varian Inova 400 MHz spectrophotometer.

Further, the high resolution mass spectrometry (HRMS) was carried out using Agilent 6220 Accurate time-of-flight LC/MS spectrometer.

Reference Example 1

5,5'-(propane-2,2-diyl)bis(2-methylfuran) was produced following the reaction scheme shown in formula (7) below.

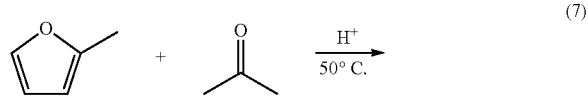

(7)

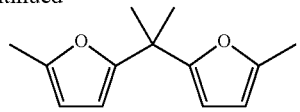

More specific explanation is made below.

Acetone (5.36 mL, 73.0 mmol) and 2-methylfuran (10.0 g, 121.8 mmol) were mixed in a 100 mL round-bottom flask at 0° C. Then, an aqueous H$_2$SO$_4$ solution (0.325 mL (6.09 mmol) of 98% H$_2$SO$_4$, previously diluted in 0.325 mL of H$_2$O) was added dropwise to the reaction mixture under stirring. Then, the flask was sealed, and the reaction mixture was further stirred for 20 h at 50° C. The reaction mixture was neutralized with a saturated aqueous NaHCO$_3$. Then, the mixture was extracted with ethyl acetate (3×100 mL), and the combined organic fractions were washed with a deionized water, dried with magnesium sulfate, filtered and concentrated under a reduced pressure. As a result, 5,5'-(propane-2,2-diyl)bis(2-methylfuran) (hereinafter, frequently referred to as "raw material compound (rm-1)") was obtained as an orange-yellow liquid (11.8 g, 95% yield).

With respect to the obtained raw material compound (rm-1), the data of $^1$H-NMR, $^{13}$C-NMR and HRMS are shown below.

$^1$H NMR (400 MHz, CDCl$_3$): δ 1.60 (s, 6H, C(CH$_3$)$_2$), 2.25 (s, 6H, CH$_3$), 5.85 (d, J=2.8 Hz, 2H, furan ring H), 5.87 (d, J=2.8 Hz, 2H, furan ring H)

$^{13}$C NMR (100 MHz, CDCl$_3$): δ 13.72, 26.60, 37.33, 104.64, 105.84, 150.63, 158.72 ppm HRMS calculated for [C$_{13}$H$_{16}$O$_2$+H]$^+$ [M+H]$^+$: m/z=205.1229, found: 205.1223

Additionally, it is worth pointing out that when 12.18 mmol (1.03 mL) of 37% HCl was used as the catalyst instead of the aforementioned aqueous H$_2$SO$_4$ solution, the raw material compound (rm-1) was obtained in a yield comparable to the case of using the aqueous H$_2$SO$_4$ solution as a catalyst. However, the aqueous H$_2$SO$_4$ solution worked slightly better for this reaction in terms of the purity of the resulting raw material compound (rm-1).

Example 1

5,5'-(propane-2,2-diyl)bis(2-(bromomethyl)furan) was produced following the reaction scheme shown in formula (8) below.

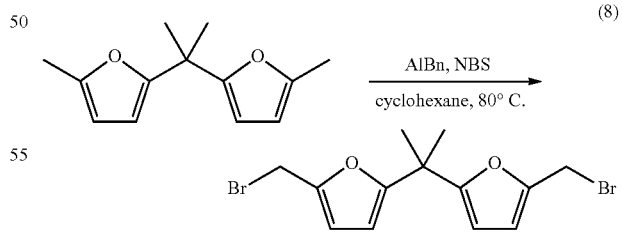

(8)

More specific explanation is made below.

To a 100 mL round-bottom flask was added cyclohexane (30 mL) solution of the raw material compound (rm-1) (2.0 g, 9.8 mmol), N-bromosuccinimide (NBS) (4.19 g, 23.5 mmol) as a halogenating agent, and azobisisobutyronitrile (AIBN) (161 mg, 0.98 mmol) as a radical initiator under nitrogen atmosphere. The mixture was stirred at 80° C. for 5 h. After the reaction, 200 mL of dichloromethane and 75 mL of deionized water were added. The mixture was stirred for about 10 min, and then phases were separated. The organic layer was further washed with deionized water three times, dried with magnesium sulfate, filtered and concentrated to dryness. As a result, 5,5'-(propane-2,2-diyl)bis(2-(bromomethyl)furan) (hereinafter, frequently referred to as "intermediate compound (i-1)") (3.54 g) was obtained quantitatively as a black viscous liquid. The obtained intermediate compound (i-1) was used directly in the subsequent reaction without further purification.

With respect to the obtained intermediate compound (i-1), the data of $^1$H-NMR and $^{13}$C-NMR are shown below.

$^1$H NMR (400 MHz, CDCl$_3$): δ 1.65 (s, 6H, C(CH$_3$)$_2$), 4.49 (s, 4H, CH$_2$Br), 5.98 (d, J=3.2 Hz, 2H, furan ring H), 6.29 (d, J=3.2 Hz, 2H, furan ring H)

$^{13}$C NMR (100 MHz, CDCl$_3$): δ 24.49, 26.29, 37.93, 106.09, 110.73, 148.92, 160.82 ppm

Example 2

5,5'-(propane-2,2-diyl)bis(furan-2-carboxylic acid) was produced following the reaction scheme shown in formula (9) below.

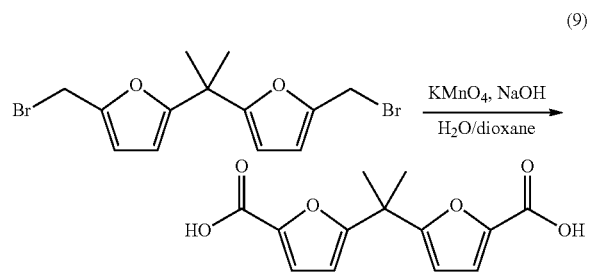

(9)

More specific explanation is made below.

To a 250 mL round-bottom flask was added NaOH (13.3 g, 332 mmol) and H$_2$O (90 mL). Under stirring at room temperature, the aforementioned intermediate compound (i-1) (2.0 g, 5.52 mmol, previously dissolved in 30 mL of 1,4-dioxane) was added to the mixture, followed by addition of KMnO$_4$ (5.24 g, 33.2 mmol). The reaction mixture was stirred at room temperature for 2 h. The precipitate of manganese oxide was filtered off, washed with deionized water. The filtrate was concentrated under pressure to remove the 1,4-dioxane solvent, and the pH of the aqueous filtrate was adjusted to <1 using 37% HCl. The manganese oxide precipitate was further washed with ethyl acetate. The ethyl acetate filtrate was mixed with the above acidified aqueous filtrate. Then, the mixture was extracted with ethyl acetate (3×100 mL). The ethyl acetate phase was dried with magnesium sulfate, filtered and concentrated under reduced pressure. As a result, 5,5'-(propane-2,2-diyl)bis(furan-2-carboxylic acid) was obtained as a pale yellow powder (1.35 g, 92% yield).

With respect to the obtained compound, the data of $^1$H-NMR, $^{13}$C-NMR and HRMS are shown below.

$^1$H NMR (400 MHz, DMSO-d$_6$): δ 1.64 (s, 6H, C(CH$_3$)$_2$), 6.42 (d, J=3.6 Hz, 2H, furan ring H), 7.14 (d, J=3.6 Hz, 2H, furan ring H)

$^{13}$C NMR (100 MHz, DMSO-d$_6$): δ 25.67, 37.59, 107.55, 118.65, 143.91, 159.26, 162.54 ppm HRMS calculated for [C$_{13}$H$_{12}$O$_6$+Na]$^+$ [M+Na]$^+$: m/z=287.0532, found: 287.0526.

Example 3

(5,5'-(propane-2,2-diyl)bis(furan-5,2-diyl))dimethanol was produced following the reaction scheme shown in formula (10) below.

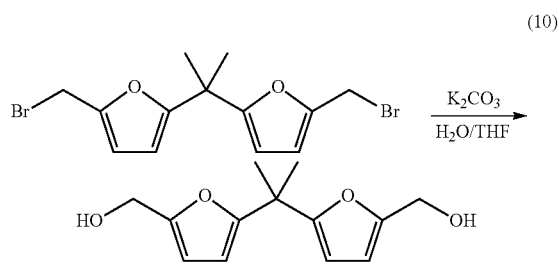

(10)

More specific explanation is made below.

To a 250 mL round-bottom flask was added K$_2$CO$_3$ (2.29 g, 16.58 mmol) and H$_2$O (50 mL). Under stirring at room temperature, the intermediate compound (i-1) (3.0 g, 8.29 mmol, previously dissolved in 50 mL of THF) was slowly added to the mixture. The reaction mixture was stirred at room temperature for 2 h. Then, the majority of THF solvent was removed under reduced pressure, and the mixture was extracted with ethyl acetate (3×80 mL). Here, the aqueous phase was saturated with NaCl for the nearly quantitative extraction of the product. The ethyl acetate phase was dried with magnesium sulfate, filtered and concentrated under reduced pressure. The crude product was further purified by silica gel column chromatography (acetone/hexanes=3/7, v/v). As a result, a purified 5,5'-(propane-2,2-diyl)bis(furan-5,2-diyl))dimethanol was obtained as a pale yellow solid (1.92 g, 98% yield).

With respect to the obtained compound, the data of $^1$H-NMR, $^{13}$C-NMR and HRMS are shown below.

$^1$H NMR (400 MHz, CDCl$_3$): δ 1.63 (s, 6H, C(CH$_3$)$_2$), 4.54 (s, 4H, CH$_2$OH), 5.97 (d, J=3.2 Hz, 2H, furan ring H), 6.18 (d, J=3.2 Hz, 2H, furan ring H)

$^{13}$C NMR (100 MHz, CDCl$_3$): 26.31, 37.44, 57.26, 104.89, 108.34, 152.92, 159.98 ppm HRMS calculated for [C$_{13}$H$_{16}$O$_4$+Na]$^+$ [M+Na]$^+$: m/z=259.0946, found: 259.0941

Example 4

2,2'-((5,5'-(propane-2,2-diyl)bis(furan-5,2-diyl))bis(methylene))bis(isoindoline-1,3-dione) was produced following the reaction scheme shown in formula (11) below.

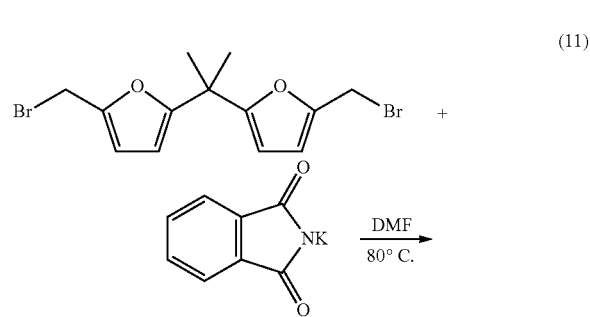

(11)

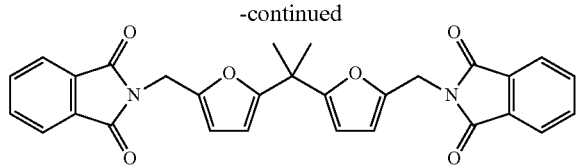

More specific explanation is made below.

To a 250 mL round-bottom flask was added potassium phthalimide (3.38 g, 18.24 mmol) and the aforementioned intermediate compound (i-1) (3.0 g, 8.29 mmol, previously dissolved in 30 mL of dry DMF) under nitrogen atmosphere. The reaction mixture was stirred at 80° C. for 12 h. After cooling to room temperature, the solution was filtered, and added to 100 mL of deionized water. The precipitate was collected, washed thoroughly with water, and dissolved in DCM. The DCM solution was dried with magnesium sulfate, filtered and concentrated under reduced pressure. As a result, 2,2'-((5,5'-(propane-2,2-diyl)bis(furan-5,2-diyl))bis(methylene))bis(isoindoline-1,3-dione) (hereinafter, frequently referred to as "intermediate compound (i-1')") was obtained as a brown powder (3.61 g, 88% yield).

With respect to the obtained intermediate compound (i-1'), the data of $^1$H-NMR and $^{13}$C-NMR are shown below.

$^1$H NMR (400 MHz, CDCl$_3$): δ 1.54 (s, 6H, CH$_3$), 4.78 (s, 4H, NCH$_2$), 5.86 (d, J=3.2 Hz, 2H, furan ring H), 6.16 (d, J=3.2 Hz, 2H, furan ring H), 7.71 (m, 4H, benzene ring H), 7.84 (m, 4H, benzene ring H)

$^{13}$C NMR (100 MHz, CDCl$_3$): δ 26.27, 34.60, 37.50, 105.26, 109.01, 123.42, 132.12, 134.03, 147.80, 159.59, 167.55 ppm Example 5

(5,5'-(propane-2,2-diyl)bis(furan-5,2-diyl))dimethanamine was produced following the reaction scheme shown in formula (12) below.

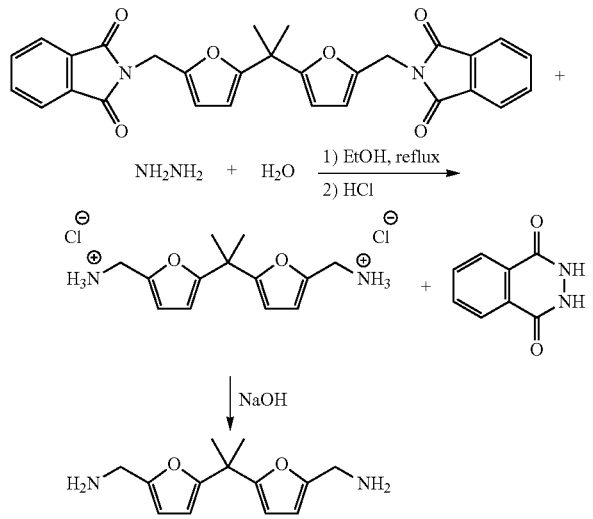

(12)

More specific explanation is made below.

To a 250 mL round-bottom flask was added the aforementioned intermediate compound (i-1') (3.0 g, 6.07 mmol), hydrazine monohydrate (1.8 g, 36 mmol) and ethanol (75 mL). The reaction mixture was stirred at reflux for 1 h. After the solution was cooled to room temperature, 37% HCl (15 mL, previously diluted with 60 mL of deionized water) was added dropwise, and the solution was stirred at refluxed for an additional 0.5 h. After cooling, the solution was filtered, and a white precipitate collected by filtration was washed with additional ethanol (50 mL). The filtrate was concentrated by rotary evaporation. The residue was dissolved in 100 mL of H$_2$O, made alkaline with NaOH pellets, and extracted with DCM (3×100 mL). Here, the aqueous phase was saturated with NaCl for the maximum extraction of the product. The DCM phase was further washed with a saturated NaCl aqueous solution, dried over magnesium sulfate, filtered and concentrated under reduced pressure. As a result, (5,5'-(propane-2,2-diyl)bis(furan-5,2-diyl))dimethanamine was obtained as an orange-red viscous liquid (1.35 g, 95% yield).

With respect to the obtained compound, the data of $^1$H-NMR, $^{13}$C-NMR and HRMS are shown below.

$^1$H NMR (400 MHz, CDCl$_3$): δ 1.61 (s, 6H, CH$_3$), 3.76 (s, 4H, CH$_2$NH$_2$), 5.90 (d, J=3.2 Hz, 2H, furan ring H), 6.01 (d, J=3.2 Hz, 2H, furan ring H)

$^{13}$C NMR (100 MHz, CDCl$_3$): δ 26.35, 37.38, 39.31, 104.60, 105.52, 155.07, 159.15 ppm HRMS calculated for [C$_{13}$H$_{18}$N$_2$O$_2$+Na]$^+$ [M+Na]$^+$: m/z=257.1266, found: 257.1261

Reference Example 2

5,5'-(cyclohexane-1,1-diyl)bis(2-methylfuran) was produced following the reaction scheme shown in formula (13) below.

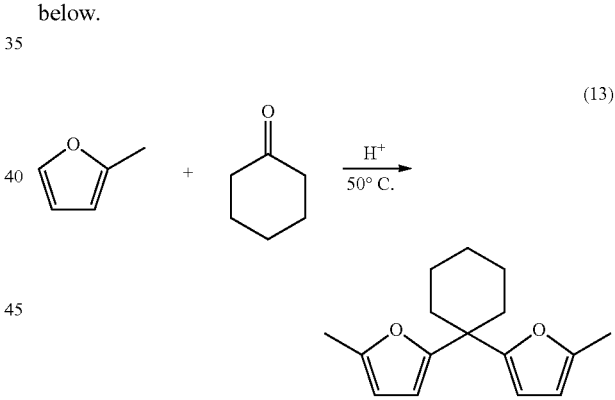

(13)

More specific explanation is made below.

Cyclohexanone (5.98 g, 60.9 mmol) and 2-methylfuran (10.0 g, 121.8 mmol) were mixed in a 100 mL round-bottom flask at 0° C. Then, an aqueous H$_2$SO$_4$ solution (0.325 mL (6.09 mmol) of 98% H$_2$SO$_4$, previously diluted in 0.325 mL of H$_2$O) was added dropwise to the reaction mixture under stirring. Then, the flask was sealed, and the reaction mixture was further stirred at 50° C. for 20 h. The reaction mixture was neutralized with saturated aqueous NaHCO$_3$. Then, the mixture was extracted with ethyl acetate (3×100 mL), and the combined organic fractions were washed with deionized water, dried with magnesium sulfate, filtered and concentrated under reduced pressure. As a result, 5,5'-(cyclohexane-1,1-diyl)bis(2-methylfuran) (hereinafter, frequently referred to as "raw material compound (rm-2)") was obtained as an orange-yellow viscous liquid (14.2 g, 95% yield).

With respect to the obtained raw material compound (rm-2), the data of $^1$H-NMR, $^{13}$C-NMR and HRMS are shown below.

$^1$H NMR (400 MHz, CDCl$_3$): δ 1.40-2.15 (m, 10H, cyclohexane ring H), 2.24 (s, 6H, CH$_3$), 5.84 (s, 4H, furan ring H)

$^{13}$C NMR (100 MHz, CDCl$_3$): δ 13.73, 22.65, 26.02, 34.10, 41.72, 105.69, 105.88, 150.31, 157.76 ppm HRMS calculated for [C$_{16}$H$_{20}$O$_2$+H]$^+$ [M+H]$^+$: m/z=245.1542, found: 245.1536

Example 6

5,5'-(cyclohexane-1,1-diyl)bis(2-(bromomethyl)furan) was produced following the reaction scheme shown in formula (14) below.

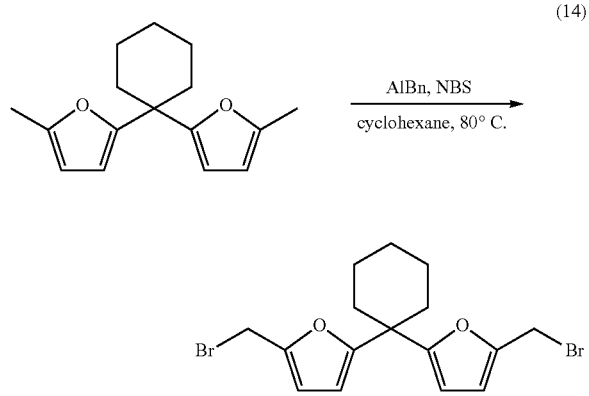

(14)

More specific explanation is made below.

To a 100 mL round-bottom flask was added cyclohexane (40 mL) solution of the aforementioned raw material compound (rm-2) (3.0 g, 12.3 mmol), NBS (5.25 g, 29.5 mmol) as a halogenating agent, and AIBN (202 mg, 1.23 mmol) as a radical initiator under nitrogen atmosphere. The mixture was stirred at 80° C. for 5 h. After the reaction, 250 mL of dichloromethane and 100 mL of deionized water were added. The mixture was stirred for about 10 min, and then phases were separated. The organic layer was further washed with deionized water three times, dried with magnesium sulfate, filtered and concentrated to dryness. As a result, 5,5'-(cyclohexane-1,1-diyl)bis(2-(bromomethyl) furan) (hereinafter, frequently referred to as "intermediate compound (i-2)") (4.93 g) was obtained quantitatively as a black solid. The obtained intermediate compound (i-2) was used directly in the subsequent reaction without further purification.

With respect to the obtained intermediate compound (i-2), the data of $^1$H-NMR and $^{13}$C-NMR are shown below.

$^1$H NMR (400 MHz, CDCl$_3$): δ 1.40-2.20 (m, 10H, cyclohexane ring H), 4.48 (s, 4H, CH$_2$Br), 5.95 (d, J=3.2 Hz, 2H, furan ring H), 6.29 (d, J=3.2 Hz, 2H, furan ring H).

$^{13}$C NMR (100 MHz, CDCl$_3$): δ 22.46, 24.61, 25.70, 33.82, 42.36, 107.11, 110.83, 148.66, 160.00 ppm.

Example 7

5,5'-(cyclohexane-1,1-diyl)bis(furan-2-carboxylic acid) was produced following the reaction scheme shown in formula (15) below.

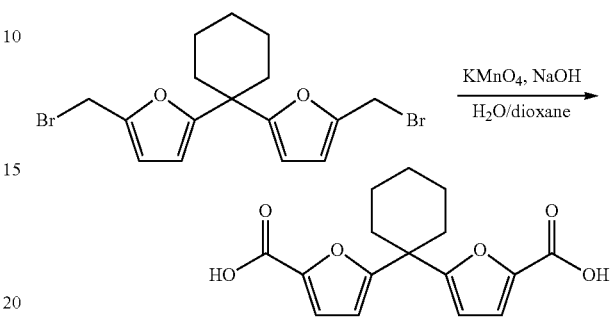

(15)

More specific explanation is made below.

To a 250 mL round-bottom flask was added NaOH (14.9 g, 373 mmol) and H$_2$O (110 mL). Under stirring at room temperature, the aforementioned intermediate compound (i-2) (2.5 g, 6.22 mmol, previously dissolved in 40 mL of 1,4-dioxane) was added to the mixture followed by KMnO$_4$ (5.89 g, 37.3 mmol). The reaction mixture was stirred at room temperature for 2 h. The precipitate of manganese oxide was filtered off, washed with deionized water. The filtrate was concentrated under pressure to remove the 1,4-dioxane solvent, and the pH of the aqueous filtrate was adjusted to <1 using 37% HCl. The manganese oxide precipitate was further washed with ethyl acetate. The ethyl acetate filtrate was mixed with the above acidified aqueous filtrate. Then, the mixture was extracted with ethyl acetate (3×100 mL). The ethyl acetate phase was dried with magnesium sulfate, filtered and concentrated under reduced pressure. As a result, 5,5'-(cyclohexane-1,1-diyl)bis(furan-2-carboxylic acid) was obtained as a pale yellow powder (1.74 g, 92% yield).

With respect to the obtained compound, the data of $^1$H-NMR, $^{13}$C-NMR and HRMS are shown below.

$^1$H NMR (400 MHz, DMSO-d$_6$): δ 1.30-2.25 (m, 10H, cyclohexane ring H), 6.41 (d, J=3.6 Hz, 2H, furan ring H), 7.14 (d, J=3.6 Hz, 2H, furan ring H)

$^{13}$C NMR (100 MHz, DMSO-d$_6$): δ 22.06, 24.97, 33.49, 41.98, 108.52, 118.80, 143.80, 159.32, 161.02 ppm HRMS calculated for [C$_{16}$H$_{16}$O$_6$+Na]$^+$ [M+Na]$^+$: m/z=327.0845, found: 327.0839

Example 8

(5,5'-(cyclohexane-1,1-diyl)bis(furan-5,2-diyl))dimethanol was produced following the reaction scheme shown in formula (16) below.

(16)

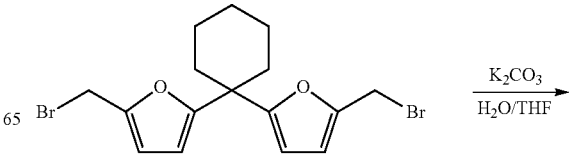

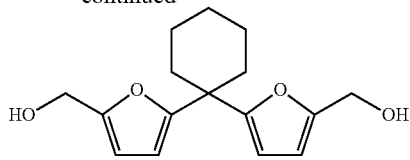

More specific explanation is made below.

To a 250 mL round-bottom flask was added K$_2$CO$_3$ (1.72 g, 12.44 mmol) and H$_2$O (40 mL). Under stirring at room temperature, the aforementioned intermediate compound (i-2) (2.5 g, 6.22 mmol, previously dissolved in 40 mL of THF) was slowly added to the mixture. The reaction mixture was stirred at room temperature for 2 h. Then, the majority of THF solvent was removed under reduced pressure, and the mixture was extracted with ethyl acetate (3×80 mL). Here, the aqueous phase was saturated with NaCl for the nearly quantitative extraction of the product. The ethyl acetate phase was dried with magnesium sulfate, filtered and concentrated under reduced pressure. The crude product was further purified by silica gel column chromatography (acetone/hexanes=3/7, v/v). As a result, a purified (5,5'-(cyclohexane-1,1-diyl)bis(furan-5,2-diyl))dimethanol was obtained as a pale yellow solid (1.69 g, 98% yield).

With respect to the obtained compound, the data of $^1$H-NMR, $^{13}$C-NMR and HRMS are shown below.

$^1$H NMR (400 MHz, CDCl$_3$): δ 1.40-2.25 (m, 10H, cyclohexane ring H), 4.54 (s, 4H, CH$_2$OH), 5.95 (d, J=3.2 Hz, 2H, furan ring H), 6.19 (d, J=3.2 Hz, 2H, furan ring H)

$^{13}$C NMR (100 MHz, CDCl$_3$): δ 22.54, 25.85, 33.91, 41.94, 57.57, 106.01, 108.50, 152.63, 159.19 ppm HRMS calculated for [C$_{16}$H$_{20}$O$_4$+Na]$^+$ [M+Na]: m/z=299.1259, found: 299.1254

Example 9

2,2'-((5,5'-(cyclohexane-1,1-diyl)bis(furan-5,2-diyl))bis(methylene))bis(isoindoline-1,3-dione) was produced following the reaction scheme shown in formula (17) below.

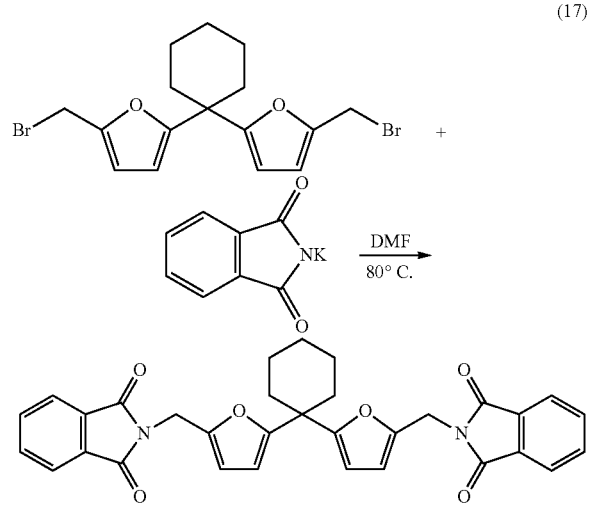

(17)

More specific explanation is made below.

To a 250 mL round-bottom flask was added potassium phthalimide (3.04 g, 16.4 mmol) and the aforementioned intermediate compound (i-2) (3.0 g, 7.46 mmol, previously dissolved in 30 mL of dry DMF) under nitrogen atmosphere. The reaction mixture was stirred at 80° C. for 12 h. After cooling to room temperature, the solution was filtered, and added to 100 mL of deionized water. The precipitate was collected, washed thoroughly with water, and dissolved in DCM. The DCM solution was dried with magnesium sulfate, filtered and concentrated under reduced pressure. As a result, 2,2'-((5,5'-(cyclohexane-1,1-diyl)bis(furan-5,2-diyl))bis(methylene))bis(isoindoline-1,3-dione) (hereinafter, frequently referred to as "intermediate compound (i-2')") was obtained as a brown powder (3.47 g, 87% yield).

With respect to the obtained intermediate compound (i-2'), the data of $^1$H-NMR and $^{13}$C-NMR are shown below.

$^1$H NMR (400 MHz, CDCl$_3$): δ 1.30-2.20 (m, 10H, cyclohexane ring H), 4.77 (s, 4H, NCH$_2$), 5.83 (d, J=3.2 Hz, 2H, furan ring H), 6.15 (d, J=3.2 Hz, 2H, furan ring H), 7.71 (m, 4H, benzene ring H), 7.86 (m, 4H, benzene ring H)

$^{13}$C NMR (100 MHz, CDCl$_3$): δ 22.37, 25.65, 33.77, 34.62, 41.87, 106.25, 109.05, 123.41, 132.13, 134.02, 147.56, 158.72, 167.57 ppm Example 10

(5,5'-(cyclohexane-1,1-diyl)bis(furan-5,2-diyl))dimethanamine was produced following the reaction scheme shown in formula (18) below.

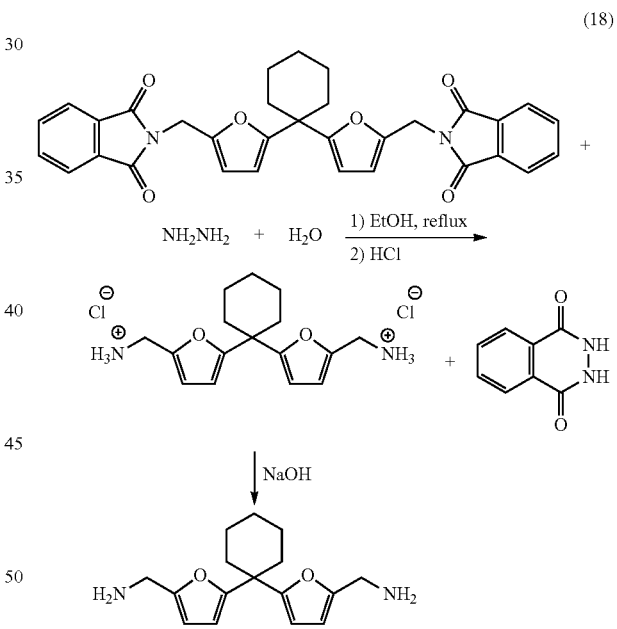

(18)

More specific explanation is made below.

To a 250 mL round-bottom flask was added the aforementioned intermediate compound (i-2') (3.0 g, 5.61 mmol), hydrazine monohydrate (1.68 g, 33.6 mmol) and ethanol (75 mL). The reaction mixture was stirred at reflux for 1 h. After the solution was cooled to room temperature, 37% HCl (15 mL, previously diluted with 60 mL of deionized water) was added dropwise, and the solution was stirred at refluxed for an additional 0.5 h. After cooling, the solution was filtered, and a white precipitate collected by filtration was washed with additional ethanol (50 mL). The filtrate was concentrated by rotary evaporation. The residue was dissolved in 100 mL of H$_2$O, made alkaline with NaOH pellets, and extracted with DCM (3×100 mL). Here, the aqueous phase was saturated with NaCl for the maximum extraction of the product. The DCM phase was further washed with a saturated NaCl aqueous solution, dried over magnesium sulfate, filtered and concentrated under reduced pressure. As a result, (5,5'-(cyclohexane-1,1-diyl)bis(furan-5,2-diyl))dimethanamine was obtained as an orange-red viscous liquid (1.46 g, 95% yield).

With respect to the obtained compound, the data of $^1$H-NMR, $^{13}$C-NMR and HRMS are shown below.

$^1$H NMR (400 MHz, CDCl$_3$): δ 1.40-2.20 (m, 10H, cyclohexane ring H), 3.77 (s, 4H, CH$_2$NH$_2$), 5.89 (d, J=3.2 Hz, 2H, furan ring H), 6.03 (d, J=3.2 Hz, 2H, furan ring H)

$^{13}$C NMR (100 MHz, CDCl$_3$): δ 22.50, 25.82, 33.92, 39.42, 41.85, 105.55, 105.66, 154.93, 158.27 ppm HRMS calculated for [C$_{16}$H$_{22}$N$_2$O$_2$+Na]$^+$ [M+Na]$^+$: m/z=297.1579, found: 297.1573

Reference Example 3

Bis(5-methylfuran-2-yl)methane was produced following the reaction scheme shown in formula (19) below.

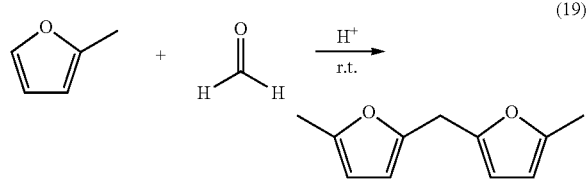

(19)

More specific explanation is made below.

Formaldehyde (FA) solution (37 wt % in water, stabilized by 10-15 wt % methanol) (10.88 mL, 146 mmol) and 2-methylfuran (20.0 g, 243.6 mmol) were mixed in a 100 mL round-bottom flask at 0° C. Then, an aqueous H$_2$SO solution (0.65 mL (12.18 mmol) of 98% H$_2$SO, previously diluted in 0.65 mL of H$_2$O) was added dropwise to the reaction mixture under stirring. Then, the flask was sealed, and the reaction mixture was further stirred for 24 h at room temperature. The reaction mixture was neutralized with saturated aqueous NaHCO$_3$. Then, the mixture was extracted with ethyl acetate (3×150 mL), and the combined organic fractions were washed with deionized water, dried with magnesium sulfate, filtered and concentrated under reduced pressure. As a result, bis(5-methylfuran-2-yl)methane (hereinafter, frequently referred to as "raw material compound (rm-3)") was obtained as an orange-red liquid (20.4 g, 95% yield).

With respect to the obtained raw material compound (rm-3), the data of $^1$H-NMR, $^{13}$C-NMR and HRMS are shown below.

$^1$H NMR (400 MHz, CDCl$_3$): δ 2.26 (s, 6H, CH$_3$), 3.89 (s, 2H, CH$_2$), 5.87 (d, J=2.8 Hz, 2H, furan ring H), 5.95 (d, J=2.8 Hz, 2H, furan ring H)

$^{13}$C NMR (100 MHz, CDCl$_3$): δ 13.62, 27.62, 106.21, 107.02, 150.09, 151.03 ppm HRMS calculated for [C$_{11}$H$_{12}$O$_2$+H]$^+$ [M+H]$^+$: m/z=177.0916, found: 177.0910

Reference Example 4

Bis(5-methylfuran-2-yl)methanone was produced following the reaction scheme shown in formula (20) below.

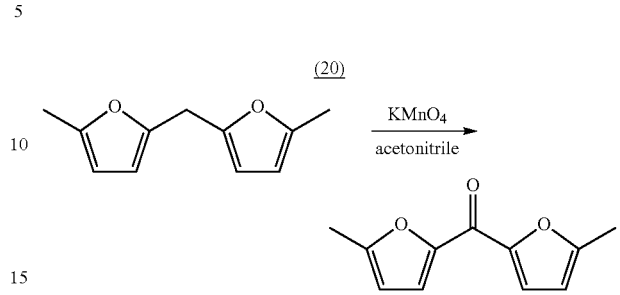

(20)

More specific explanation is made below.

To a solution of the raw material compound (rm-3) (2.0 g, 11.3 mmol) in acetonitrile (80 mL) was added KMnO$_4$ (10.7 g, 67.8 mmol) portionwise over 15 min. The mixture was stirred vigorously at room temperature for 3 h. The reaction mixture was filtered and the residue was washed with dichloromethane. The filtrate was dried with magnesium sulfate, filtered and concentrated under reduced pressure. As a result, bis(5-methylfuran-2-yl)methanone (hereinafter, frequently referred to as "raw material compound (rm-3')") was obtained as an orange-yellow viscous liquid (0.54 g, 25% yield).

With respect to the obtained intermediate compound (i-3'), the data of $^1$H-NMR and $^{13}$C-NMR are shown below.

$^1$H NMR (400 MHz, CDCl$_3$): δ 2.44 (s, 6H, CH$_3$), 6.20 (d, J=3.6 Hz, 2H, furan ring H), 7.41 (d, J=3.6 Hz, 2H, furan ring H)

$^{13}$C NMR (100 MHz, CDCl$_3$): δ 14.10, 109.08, 120.88, 150.32, 157.74, 167.90 ppm Example 11

Bis(5-(bromomethyl)furan-2-yl)methanone was produced (through the aforementioned raw material compound (rm-3')) following the reaction scheme shown in formula (21) below.

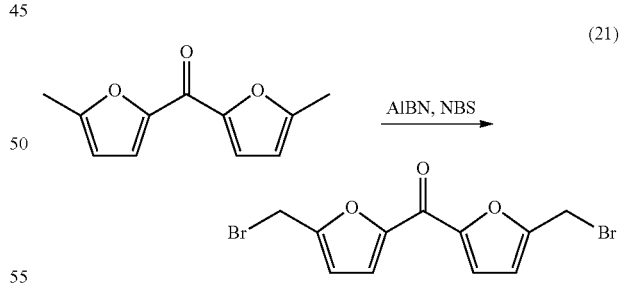

(21)

More specific explanation is made below.

To a 100 mL round-bottom flask was added benzene (30 mL) solution of the aforementioned raw material compound (rm-3') (1.2 g, 6.3 mmol), NBS (2.69 g, 15.1 mmol) as a halogenating agent, and AIBN (103.5 mg, 0.63 mmol) as a radical initiator under nitrogen atmosphere. The mixture was stirred at 80° C. for 5 h. After the reaction, 150 mL of dichloromethane and 75 mL of deionized water were added. The mixture was stirred for about 10 min, and then phases were separated. The organic layer was further washed with deionized water three times, dried with magnesium sulfate, filtered and concentrated to dryness. As a result, bis(5-(bromomethyl)furan-2-yl)methanone (hereinafter, frequently referred to as "intermediate compound (i-3)") was obtained as an orange-red liquid (2.15 g, 98% yield).

With respect to the obtained intermediate compound (i-3), the data of $^1$H-NMR is shown below.

$^1$H NMR (400 MHz, CDCl$_3$): δ 4.54 (s, 4H, CH$_2$Br), 6.60 (d, J=3.6 Hz, 2H, furan ring H), 7.51 (d, J=3.6 Hz, 2H, furan ring H)

The invention claimed is:

1. A bisfuran dihalide of the following formula (1):

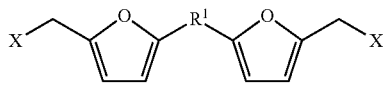

(1)

wherein R$^1$ is a divalent hydrocarbon group of the formula —CR$^2$R$^3$— (wherein each of R$^2$ and R$^3$ independently represents a hydrogen atom or a monovalent hydrocarbon group, and R$^2$ and R$^3$ may together form a cyclic structure); and each X independently represents a halogen atom.

2. The bisfuran dihalide according to claim 1, wherein each of R$^2$ and R$^3$ is independently a monovalent hydrocarbon group.

3. The bisfuran dihalide according to claim 1, wherein each X is a bromine atom.

4. A method for producing the bisfuran dihalide of claim 1, comprising reacting a bisfuran of the following formula (2) and a halogenating agent:

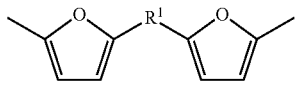

(2)

wherein R$^1$ is a divalent hydrocarbon group of the formula —CR$^2$R$^3$— (wherein each of R$^2$ and R$^3$ independently represents a hydrogen atom or a monovalent hydrocarbon group, and R$^2$ and R$^3$ may together form a cyclic structure).

5. A method for producing a bisfuran diacid of the following formula (3), comprising oxidizing the bisfuran dihalide of claim 1:

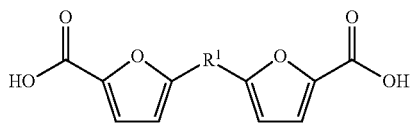

(3)

wherein R$^1$ is a divalent hydrocarbon group of the formula —CR$^2$R$^3$— (wherein each of R$^2$ and R$^3$ independently represents a hydrogen atom or a monovalent hydrocarbon group, and R$^2$ and R$^3$ may together form a cyclic structure).

6. A method for producing a bisfuran diol of the following formula (4), comprising hydrolyzing the bisfuran dihalide of claim 1:

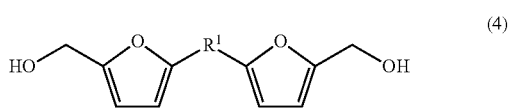

(4)

wherein R$^1$ is a divalent hydrocarbon group of the formula —CR$^2$R$^3$— (wherein each of R$^2$ and R$^3$ independently represents a hydrogen atom or a monovalent hydrocarbon group, and R$^2$ and R$^3$ may together form a cyclic structure).

7. A method for producing a bisfuran diamine of the following formula (5), comprising using the bisfuran dihalide of claim 1 as a starting material:

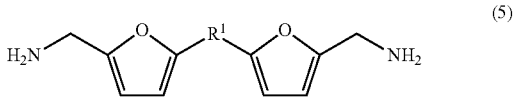

(5)

wherein R$^1$ is a divalent hydrocarbon group of the formula —CR$^2$R$^3$— (wherein each of R$^2$ and R$^3$ independently represents a hydrogen atom or a monovalent hydrocarbon group, and R$^2$ and R$^3$ may together form a cyclic structure).

8. A method for producing the bisfuran dihalide of claim 2, comprising reacting a bisfuran of the following formula (2) and a halogenating agent:

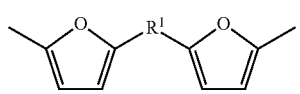

(2)

wherein R$^1$ is a divalent hydrocarbon group of the formula —CR$^2$R$^3$— (wherein each of R$^2$ and R$^3$ independently represents a monovalent hydrocarbon group.

9. A method for producing the bisfuran dihalide of claim 3, comprising reacting a bisfuran of the following formula (2) and a halogenating agent:

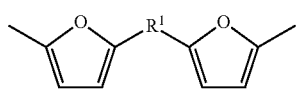

(2)

wherein R$^1$ is a divalent hydrocarbon group of the formula —CR$^2$R$^3$— (wherein each of R$^2$ and R$^3$ independently represents a hydrogen atom or a monovalent hydrocarbon group, and R$^2$ and R$^3$ may together form a cyclic structure).

10. A method for producing a bisfuran diacid of the following formula (3), comprising oxidizing the bisfuran dihalide of claim 2:

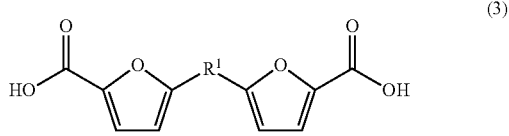

(3)

wherein $R^1$ is a divalent hydrocarbon group of the formula —$CR^2R^3$— (wherein each of $R^2$ and $R^3$ independently represents a monovalent hydrocarbon group.

11. A method for producing a bisfuran diacid of the following formula (3), comprising oxidizing the bisfuran dihalide of claim 3:

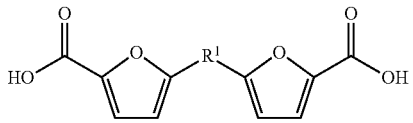

(3)

wherein $R^1$ is a divalent hydrocarbon group of the formula —$CR^2R^3$— (wherein each of $R^2$ and $R^3$ independently represents a hydrogen atom or a monovalent hydrocarbon group, and $R^2$ and $R^3$ may together form a cyclic structure).

12. A method for producing a bisfuran diol of the following formula (4), comprising hydrolyzing the bisfuran dihalide of claim 2:

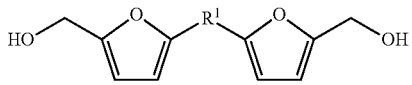

(4)

wherein $R^1$ is a divalent hydrocarbon group of the formula —$CR^2R^3$— (wherein each of $R^2$ and $R^3$ independently represents a monovalent hydrocarbon group.

13. A method for producing a bisfuran diol of the following formula (4), comprising hydrolyzing the bisfuran dihalide of claim 3:

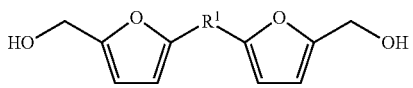

(4)

wherein $R^1$ is a divalent hydrocarbon group of the formula —$CR^2R^3$— (wherein each of $R^2$ and $R^3$ independently represents a hydrogen atom or a monovalent hydrocarbon group, and $R^2$ and $R^3$ may together form a cyclic structure).

14. A method for producing a bisfuran diamine of the following formula (5), comprising using the bisfuran dihalide of claim 2 as a starting material:

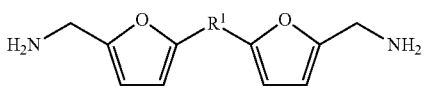

(5)

wherein $R^1$ is a divalent hydrocarbon group of the formula —$CR^2R^3$— (wherein each of $R^2$ and $R^3$ independently represents a monovalent hydrocarbon group.

15. A method for producing a bisfuran diamine of the following formula (5), comprising using the bisfuran dihalide of claim 3 as a starting material:

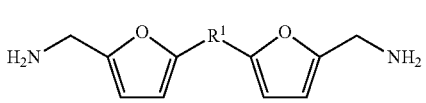

(5)

wherein $R^1$ is a divalent hydrocarbon group of the formula —$CR^2R^3$— (wherein each of $R^2$ and $R^3$ independently represents a hydrogen atom or a monovalent hydrocarbon group, and $R^2$ and $R^3$ may together form a cyclic structure).

\* \* \* \* \*